(12) United States Patent
Potgeter et al.

(10) Patent No.: US 9,370,178 B2
(45) Date of Patent: Jun. 21, 2016

(54) ANIMAL REPELLANT AND ASSOCIATED DISPENSER

(75) Inventors: Joel D. Potgeter, West Olive, MI (US); Michael A. Rose, Hudsonville, MI (US); David L. Ver Burg, Dorr, MI (US); John E. Bramer, Grandville, MI (US)

(73) Assignee: Deer on a String, Inc., Dorr, MI (US)

( * ) Notice: Subject to any disclaimer, the term of this patent is extended or adjusted under 35 U.S.C. 154(b) by 589 days.

(21) Appl. No.: 12/290,954

(22) Filed: Nov. 5, 2008

(65) Prior Publication Data

US 2009/0060964 A1    Mar. 5, 2009

Related U.S. Application Data

(63) Continuation-in-part of application No. 11/801,604, filed on May 10, 2007, now Pat. No. 8,889,116.

(51) Int. Cl.
| | | |
|---|---|---|
| A01N 25/34 | (2006.01) |
| A01N 25/18 | (2006.01) |
| A01N 63/02 | (2006.01) |
| A01P 17/00 | (2006.01) |

(52) U.S. Cl.
CPC ............... *A01N 25/18* (2013.01); *A01N 25/34* (2013.01); *A01N 63/02* (2013.01)

(58) Field of Classification Search
None
See application file for complete search history.

(56) References Cited

U.S. PATENT DOCUMENTS

| | | | | |
|---|---|---|---|---|
| 4,029,113 A | * | 6/1977 | Guyton | 132/321 |
| 4,451,460 A | * | 5/1984 | Hansen et al. | 514/170 |
| 4,818,535 A | * | 4/1989 | Baines et al. | 424/407 |
| 5,680,875 A | * | 10/1997 | Winters | 132/324 |
| 5,765,576 A | * | 6/1998 | Dolan et al. | 132/321 |
| 5,765,739 A | | 6/1998 | Yates, III | |
| 5,806,666 A | | 9/1998 | Chiang et al. | |
| 5,996,928 A | | 12/1999 | Whitehorse-Burns | |
| 6,295,996 B1 | | 10/2001 | Dickie | |
| 6,295,997 B1 | | 10/2001 | Dickie | |
| 6,302,121 B1 | * | 10/2001 | McConnell | 132/321 |
| 6,488,036 B1 | | 12/2002 | Francis | |
| 2004/0048231 A1 | * | 3/2004 | Perlin | 434/263 |
| 2007/0119475 A1 | * | 5/2007 | Hudnall et al. | 132/321 |
| 2009/0277972 A1 | * | 11/2009 | Kennon et al. | 239/6 |

OTHER PUBLICATIONS

Klappenbach, How Many Animal Cpecies Inhabit Our Planet, About. com(2014)[online], [retrieved on Aug. 20, 2014]. Retrieved from the Internet <URL:http://animals.about.com/od/zoologybasics/a/howmanyspecies.htm?p=1>, pp. 1, 2.*
Mammals (2014), [online], [retrieved on Aug. 20, 2014]. Retrieved from the Internet <URL:http://readyed.com.au/Sites/zoo/mammal.htm>, pp. 1-5.*
Hengemihle, Dealing with Nuisance Wildlife, University of Maryland Extension and The Home and Garden Information Center (2005), pp. 1-6.*
"Scent Free Secrets", Wildlife Research Center (2006), pp. 1-32.*

* cited by examiner

*Primary Examiner* — Abigail Fisher
*Assistant Examiner* — Frank Choi
(74) *Attorney, Agent, or Firm* — King & Partners, PLC

(57) ABSTRACT

A dispenser for an animal repellant including: a housing, wherein the housing includes a chamber for containing a spool; a spool, wherein the spool is associated with the chamber of the housing, and wherein the spool is associated with an animal repellant; and wherein the animal repellant includes a substrate, wherein the substrate is associated with an agent wherein the agent includes an animal repellant.

3 Claims, 2 Drawing Sheets

ANIMAL REPELLANT AND ASSOCIATED DISPENSER

CROSS-REFERENCE TO RELATED APPLICATION(S)

This application is a continuation-in-part of U.S. application Ser. No. 11/801,604, filed May 10, 2007 now U.S. Pat. No. 8,889,116, which is hereby incorporated herein by reference in its entirety—including all references cited therein.

BACKGROUND OF THE INVENTION

1. Field of the Invention

The present invention relates in general to animal repellants and, more particularly, to an animal repellant that includes a substrate and an animal repelling agent which is preferably associated with a dispenser.

2. Background Art

Gardening, landscaping, and maintaining horticulture have been prevalent in society worldwide for centuries. Indeed, gardening, landscaping, and maintaining horticulture is extremely popular in the United States—especially in the Midwestern states where a large variety of vegetative species can be optimally cultivated. While homes with gardens and landscapes have become increasingly popular in today's society, keeping destructive animals out of such areas remains problematic.

Traditionally owners of gardens and landscapes erect one or more fences to keep unwanted animals from eating and, in turn, destroying trees, shrubs, bushes, plants, flowers, grasses, vegetation, etcetera. However, fences are generally unsightly and can be expensive to erect and/or maintain. In fact, in many areas of the United States fences are strictly prohibited.

Other attempts to preclude unwanted animals from entering gardens and horticultural areas include liquid repellants which can be sprayed onto the trees, shrubs, bushes, plants, flowers, grasses, and vegetation and/or solid, granular repellants which can be dispensed on the ground of the garden or landscape.

Liquid repellants are undesirable for a plurality of reasons, including, among others, difficulty associated with repellant storage, spilling, and/or post application removal, as well as toxicity to workers and observers of the garden or horticultural areas. In fact, wind and other climate conditions can render dispensing liquid animal repellant problematic if not futile—especially in gusty conditions where the gardener may get dosed with repellant from wind shear. For many gardeners, getting dosed with repellant can substantially diminish the satisfaction of the overall gardening experience—especially for those gardeners who are susceptible to headaches from the pungent aroma of urea based liquids.

Solid, granular repellants are also undesirable for a plurality of reasons, including, among others, difficulty associated with repellant storage, spilling, and/or post application removal, as well as toxicity to workers and observers of the garden or horticultural areas from repellant dust formation.

Accordingly, it is an object of the present invention, among others, to provide an animal repellant and associated dispenser which overcomes the aforementioned problems associated with storing, dispensing, and/or utilizing, for example, conventional liquid and/or granular animal repellants.

These and other objects of the present invention will become apparent in light of the present specification, claims, and drawings.

SUMMARY OF THE INVENTION

In one embodiment, the present invention is directed to an animal repellant, comprising: (a) a substrate, wherein the substrate is associated with an agent; and (b) wherein the agent comprises an animal repellant.

In a preferred embodiment of the present invention, the substrate is impregnated (e.g. infused, soaked, steeped, saturated, drenched, permeated, pervaded, suffused, imbued, etcetera) with the agent.

In another preferred embodiment of the present invention, the substrate comprises at least one of natural and synthetic fibers. Natural fibers may include cotton, wool, linen, jute, flax, ramie, sisal, hemp, and mixtures thereof—just to name a few. Synthetic fibers may include rayon, nylon, polyester, SARAN, spandex, vinalon, NOMEX, KEVLAR, TWARON, lyocell, ZYLON, VECTRAN, and mixtures thereof—among many other fibers.

In yet another preferred embodiment of the present invention, the substrate comprises floss, such as, but not limited to, those utilized in dental and/or medical applications. In this embodiment the floss may be fabricated from silk, nylon, and/or polytetrafluoroethylene, and combinations thereof—as well as numerous other materials.

In another aspect of the present invention, the agent or animal repellant preferably comprises at least one of natural and/or synthetic predator urine, predator blood, predator hair, and predator skin—including those from reptiles, mammals, fish, birds, and/or amphibians.

In accordance with the present invention, predators may include, but are not limited to, alligator, armadillo, bear, bobcat, cougar, coyote, crocodile, elk, fox, human, lion, mouse, mink, mole, moose, muskrat, opossum, primate, raccoon, rodent, skunk, squirrel, tiger, vole, wolf, and wild boar.

In another aspect of the present invention, the agent and/or the substrate may be augmented with a secondary animal repellant, such as an agent that is tastefully offensive to the desired animal.

In yet another aspect of the present invention, at least a portion of the floss is at least partially covered with a wax.

In one embodiment, the present invention is also directed to a dispenser for an animal repellant, comprising: (a) a housing, wherein the housing includes a chamber for containing a spool; (b) a spool, wherein the spool is associated with the chamber of the housing; and (c) an animal repellant as disclosed herein, wherein the animal repellant is associated with the spool.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted. It will be further understood that the invention is not necessarily limited to the particular embodiments illustrated herein.

The invention will now be described with reference to the drawings wherein.

DETAILED DESCRIPTION OF THE INVENTION

Figure 1:
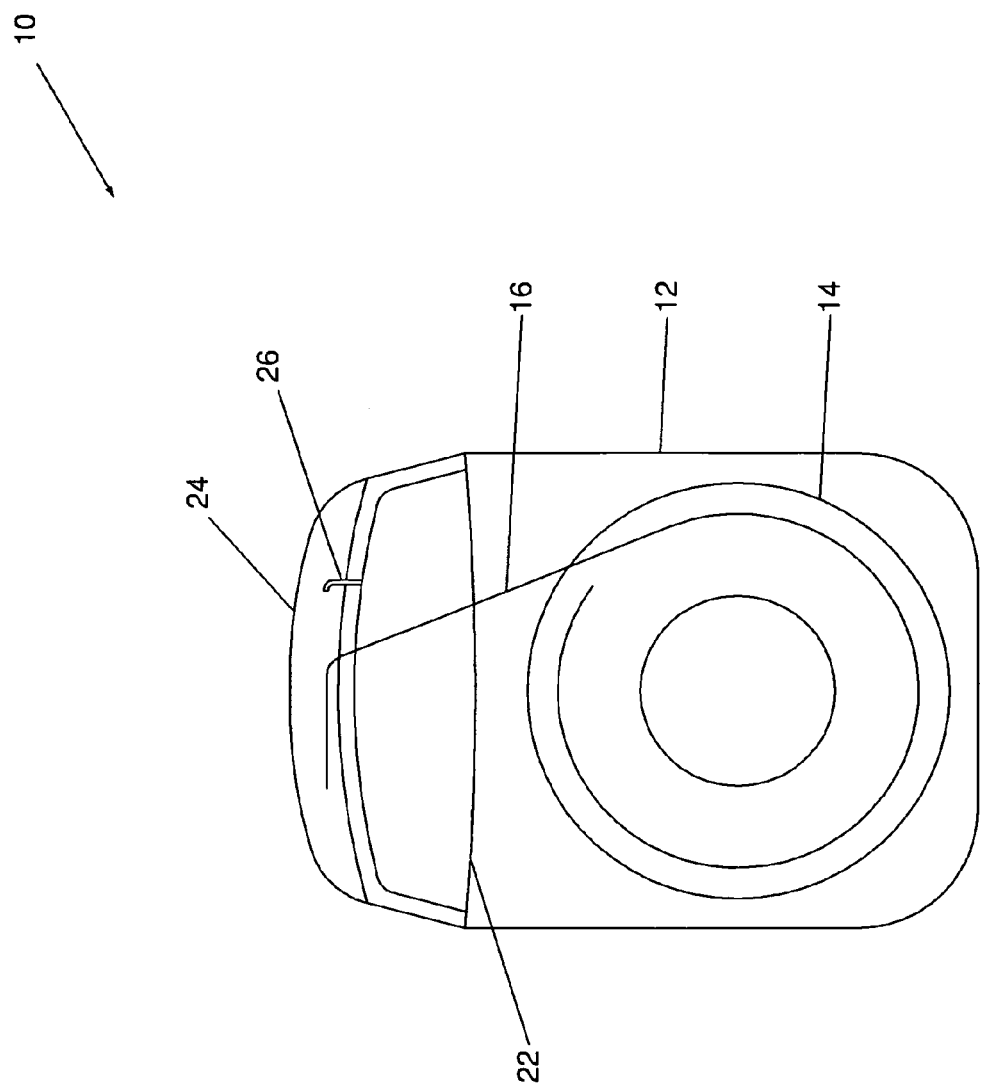
FIG. 1 is a perspective representation of an animal repellant dispenser fabricated in accordance with the present invention.

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings with like reference characters.

Figure 2:
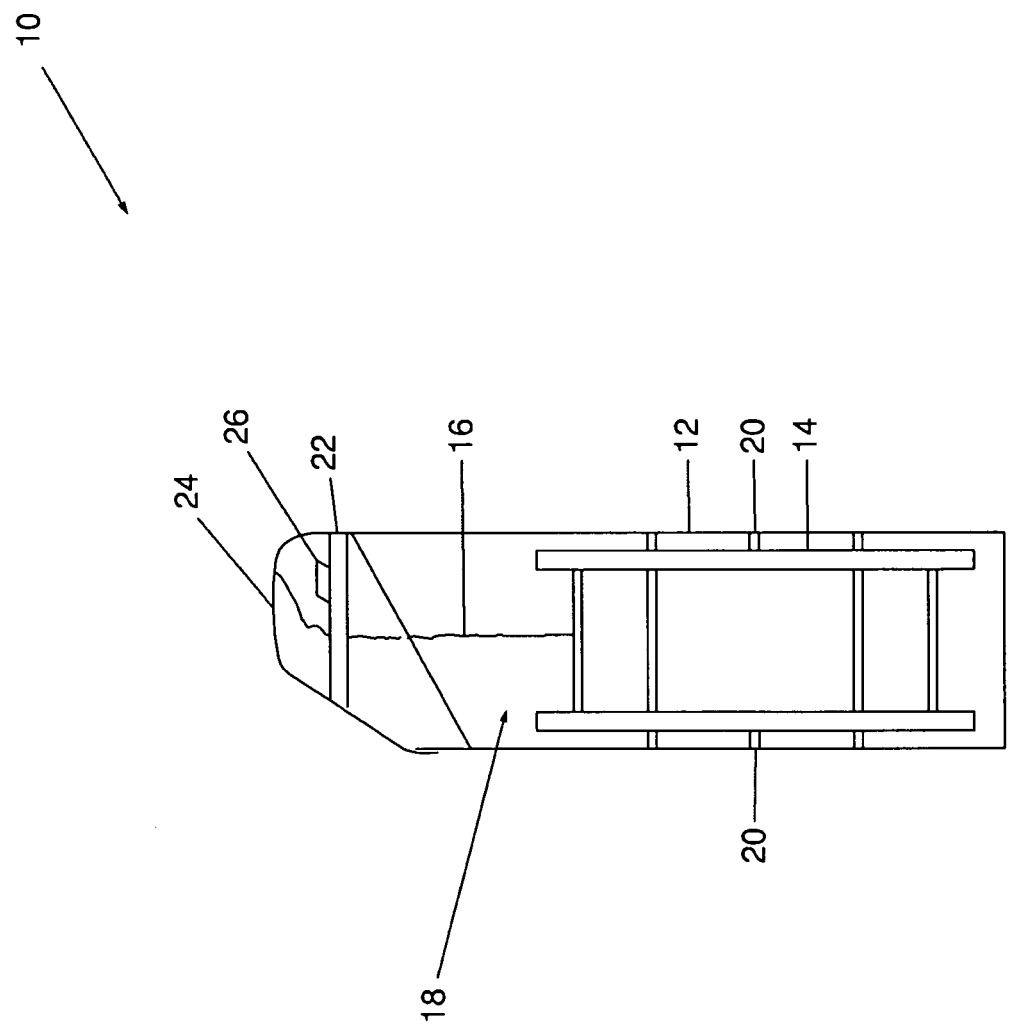
FIG. 2 is a cross-sectional representation of an animal repellant dispenser fabricated in accordance with the present invention.

Referring now to the drawings and to FIGS. 1 and 2 collectively, animal repellant dispenser 10 is shown, which generally comprises housing 12, spool 14, and animal repellant 16. As will be explained in greater detail below, it will be understood that, during normal use of animal dispenser 10, a gardener can store and dispense a repellant (e.g. an odor and/or taste repellant) without the drawbacks disclosed supra. It will be understood that the above-identified Figures are merely schematic representations of animal repellant dispenser 10. As such, some of the components may have been distorted from their actual scale for pictorial clarity.

Housing 12 of animal repellant dispenser 10 preferably includes chamber 18 for containing spool 14. Housing 12 is preferably at least substantially sealed to prevent any odor from emanating therefrom. While housing 12 has been disclosed in an embodiment herein, it will be understood that housing 12 may be configured in a analogous manner to any one of a number of dental floss type dispensers, including those disclosed in U.S. Pat. No. 5,765,739, U.S. Pat. No. 5,806,666, U.S. Pat. No. 5,996,928, U.S. Pat. No. 6,295,996, U.S. Pat. No. 6,295,997, U.S. Pat. No. 6,302,121, and U.S. Pat. No. 6,488,036—all of which are hereby incorporated herein by reference in their entirety including the references cited therein. Housing 12 is preferably fabricated from a natural and/or synthetic plastic resin. However, any one of a number of materials that would be known to those having ordinary skill in the art with the present disclosure before them are likewise contemplated for use.

Spool 14 of animal repellant dispenser 10 is associated with chamber 18. As will be discussed in greater detail below, spool 14 is associated with an animal repellant and serves to releasably retain the same in a generally reeled configuration. Spool 14 is preferably secured to housing 12 in such a manner that it is substantially free to rotate upon dispensing of an animal repellant. In one embodiment spool 14 includes tabs 20 which are received in mating slots of housing 12. It will be understood that a reciprocal configured is likewise contemplated for use in accordance with the present invention wherein spool 14 includes slots for receiving tabs associated with housing 12.

In one embodiment of the present invention, animal repellant dispenser 10 includes living hinge 22 which enables top 24 of dispenser 10 to be manipulated to and/or from an open and/or closed position while being fixedly attached to dispenser 10 along at least one seam. It will be understood that when top 24 is in a closed position, animal repellant dispenser 10 is preferably substantially sealed in such a manner that odors are substantially precluded from emanating therefrom.

In another embodiment of the present invention, animal repellant dispenser 10 includes knife 26 which enables a substrate of animal repellant 16 to be rapidly cut to any desired length. It will be understood that regardless of its ordinary meaning the term "knife" includes any member and/or object which is capable of cutting the substrate of animal repellant 16 to any desired length.

Animal repellant 16 of animal repellant dispenser 10 is preferably associated with spool 14, and comprises a substrate, wherein the substrate is associated with an agent, wherein the agent comprises an animal repellant.

In a preferred embodiment of the present invention, the substrate is impregnated (e.g. infused, soaked, steeped, saturated, drenched, permeated, pervaded, suffused, imbued, etcetera) with the agent.

In one aspect of the present invention, the substrate may comprise natural and/or synthetic fibers. Non-limiting examples of natural fibers include, cotton, wool, linen, jute, flax, ramie, sisal, hemp, and mixtures thereof—just to name a few. Non-limiting examples of synthetic fibers include rayon, nylon, polyester, SARAN, spandex, vinalon, NOMEX, KEVLAR, TWARON, lyocell, ZYLON, VECTRAN, and mixtures thereof.

In another embodiment of the present invention, the substrate comprises floss. The floss may be fabricated from, for example, silk, nylon, and/or polytetrafluoroethylene, and combinations thereof.

In accordance with the present invention the agent preferably includes one or more of predator urine, (e.g. natural and/or synthetic) predator blood, predator hair, and predator skin—including those of reptiles, mammals, fish, birds, and/or amphibians. For example, the agent may comprise urine of one or more of alligator, armadillo, bear, bobcat, cougar, coyote, crocodile, elk, fox, human, lion, mice, mink, mole, moose, muskrat, opossum, primate, raccoon, rodent, skunk, squirrel, tiger, vole, wolf, and wild boar.

An augmentant may also be associated with (e.g. impregnated) the substrate, such as a secondary animal repellant that is tastefully offensive to the desired animal.

In another aspect of the present invention, at least a portion of the substrate may be at least partially covered with a wax. Such a coating can control the intensity of an associated odor, as well as preserve the integrity of the odor and/or substrate.

In operation, a user can rapidly dispense the animal repellant while in the garden and/or landscape without concern regarding spilling and/or spraying the repellant. In addition, the repellant can be quickly attached and/or secured to tree branches, bushes, etcetera, and rapidly removed—if desired. Indeed, such a repellant alleviates the problems associated with conventional repellants as disclosed herein.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. An animal repellant dispenser, comprising:
 a housing, wherein the housing includes a front wall, a back wall, a first side wall, a second side wall, a bottom wall, and a top wall positioned in a spaced-apart relationship to define a chamber for containing a spool therein, wherein the front wall includes a first slot adapted to receive a first spool tab, and wherein the back wall includes a second slot adapted to receive a second spool tab;
 a living hinge formed between the top wall and the back wall;
 a knife adapted to cut a substrate, wherein the knife is positioned proximate the top wall of the housing;
 a spool, wherein the spool includes a first spool tab and a second spool tab, wherein the first spool tab is releasably inserted into the first slot of the front wall and the second spool tab is releasably inserted into the second slot of the back wall; and
 a substrate, wherein the substrate comprises floss and is positioned around the spool and wherein the substrate is associated with an agent, wherein the agent comprises an animal repellant, and wherein the animal repellant comprises wolf urine, cougar urine, and fox urine.

2. An animal repellant dispenser, comprising:
a housing, wherein the housing includes a front wall, a back wall, a first side wall, a second side wall, a bottom wall, and a top wall positioned in a spaced-apart relationship to define a chamber for containing a spool therein, wherein the front wall includes a first slot adapted to receive a first spool tab, and wherein the back wall includes a second slot adapted to receive a second spool tab;
a living hinge formed between the top wall and the back wall;
a knife adapted to cut a substrate, wherein the knife is positioned proximate the top wall of the housing;
a spool, wherein the spool includes a first spool tab and a second spool tab, wherein the first spool tab is releasably inserted into the first slot of the front wall and the second spool tab is releasably inserted into the second slot of the back wall; and
a substrate, wherein the substrate is positioned around the spool and wherein the substrate is associated with an agent, wherein the agent comprises an animal repellant, and wherein the animal repellant comprises urine of at least one of alligator, bear, bobcat, chipmunk, cougar, coyote, crocodile, animal, elk, fox, groundhog, human, lion, mice, mink, moose, muskrat, opossum, rabbit, raccoon, rodent, skunk, squirrel, tiger, woodchuck, wolf, wild boar, and combinations thereof.

3. An animal repellant dispenser, consisting of:
a housing, wherein the housing includes a front wall, a back wall, a first side wall, a second side wall, a bottom wall, and a top wall positioned in a spaced-apart relationship to define a chamber for containing a spool therein, wherein the front wall includes a first slot adapted to receive a first spool tab, and wherein the back wall includes a second slot adapted to receive a second spool tab;
a living hinge formed between the top wall and the back wall;
a knife adapted to cut a substrate, wherein the knife is positioned proximate the top wall of the housing;
a spool, wherein the spool includes a first spool tab and a second spool tab, wherein the first spool tab is releasably inserted into the first slot of the front wall and the second spool tab is releasably inserted into the second slot of the back wall; and
a substrate, wherein the substrate is positioned around the spool and wherein the substrate is associated with an agent, wherein the agent comprises an animal repellant, and wherein the animal repellant comprises urine of at least one of alligator, bear, bobcat, chipmunk, cougar, coyote, crocodile, animal, elk, fox, groundhog, human, lion, mice, mink, moose, muskrat, opossum, rabbit, raccoon, rodent, skunk, squirrel, tiger, woodchuck, wolf, wild boar, and combinations thereof.

* * * * *